United States Patent [19]
Cherksey

[11] Patent Number: 5,750,103
[45] Date of Patent: May 12, 1998

[54] METHOD FOR TRANSPLANTING CELLS INTO THE BRAIN AND THERAPEUTIC USES THEREFOR

[75] Inventor: Bruce D. Cherksey, Hoboken, N.J.

[73] Assignee: The New York University Medical Center, New York, N.Y.

[21] Appl. No.: 460,700

[22] Filed: Jun. 2, 1995

Related U.S. Application Data

[62] Division of Ser. No. 91,629, Jul. 13, 1993, Pat. No. 5,618,531, which is a continuation of Ser. No. 823,654, Jan. 23, 1992, abandoned, which is a continuation-in-part of Ser. No. 599,802, Oct. 19, 1990, abandoned.

[51] Int. Cl.$^6$ .............................. A61K 9/14; A61K 35/12; A61M 5/178; C12N 11/00
[52] U.S. Cl. ..................... 424/93.21; 424/93.7; 424/484; 424/486; 424/487; 424/488; 424/499; 424/500; 424/501; 435/176; 435/177; 435/178; 435/179; 435/180; 435/304.1; 435/307.1; 435/325; 435/371; 435/374; 435/395; 435/403; 435/346; 435/366; 435/368; 435/369; 604/57
[58] Field of Search .............................. 435/240.2, 69.1, 435/71.1, 176, 177, 178, 179, 180, 181, 182, 283.1, 307.1, 309.1, 325, 346, 366, 368, 369, 371, 374, 395, 403, 304.1; 424/93.21, 484, 485, 486, 487, 488, 489, 499, 500, 501, 570, 93.1, 93.2, 93.7, 93.71, 93.72, 93.73; 604/57, 187, 891.1

[56] References Cited

U.S. PATENT DOCUMENTS

| | | | |
|---|---|---|---|
| 3,974,526 | 8/1976 | Darik et al. | 623/1 |
| 4,335,215 | 6/1982 | Tolbert et al. | 435/240.24 |
| 4,458,678 | 7/1984 | Yannas et al. | 602/48 |
| 4,505,266 | 3/1985 | Yannas et al. | 128/893 |
| 4,520,821 | 6/1985 | Schmidt et al. | 606/151 |
| 4,553,272 | 11/1985 | Mears | 623/1 |
| 4,576,608 | 3/1986 | Homsy | 623/11 |
| 4,642,120 | 2/1987 | Nevo et al. | 623/16 |
| 4,645,669 | 2/1987 | Reid | 435/240.23 |
| 4,721,096 | 1/1988 | Naughton et al. | 128/898 |
| 4,748,121 | 5/1988 | Beaver et al. | 435/176 |
| 4,892,538 | 1/1990 | Aebisher | 424/424 |

(List continued on next page.)

FOREIGN PATENT DOCUMENTS

| | | |
|---|---|---|
| 0 213 908 A2 | 3/1987 | European Pat. Off. . |
| 0 339 607 A2 | 11/1989 | European Pat. Off. . |
| 28 53 614 A1 | 7/1979 | Germany . |
| WO 83/04177 | 12/1983 | WIPO . |
| WO 90/02580 | 3/1990 | WIPO . |
| WO 93/00128 | 1/1993 | WIPO . |

OTHER PUBLICATIONS

Aebischer et al., 1988, "Transplantation of neural tissue in polymer capsules," Brain Research 448:364–368.

Aebischer et al., 1991, "Long-term cross-species brain transplantation of a polymer-encapsulated dopamine-secreting cell line," Exp. Neurol. 111:269–275.

(List continued on next page.)

*Primary Examiner*—Jeffrey E. Russel
*Attorney, Agent, or Firm*—Pennie & Edmonds LLP

[57] ABSTRACT

A method for grafting a cell in the brain of a mammalian subject is accomplished by attaching the cell to a support matrix so that the cell attaches to the matrix surface, and implanting the support matrix with the attached cell into the brain. A syringe containing viable cells that are attached to a matrix surface may be used to transplant the cells into the brain or spinal cord of a mammalian subject. Preferred support matrices are glass or plastic microbeads, either solid or porous, having a diameter from about 90 to about 125 μm. The method employs cells of different types, preferably cells of neural or paraneural origin, such as adrenal chromaffin cells. Also useful are cell lines grown in vitro. Cells not of neural or paraneural origin, such as fibroblasts, may also be used following genetic alteration to express a desired neural product such as a neurotransmitter or a neuronal growth factor. The method is used to treat neurological diseases such as Parkinson's disease, Alzheimer's disease, Huntington's disease, epilepsy, and traumatic brain injury.

11 Claims, 4 Drawing Sheets

U.S. PATENT DOCUMENTS

| | | | |
|---|---|---|---|
| 4,900,553 | 2/1990 | Silver et al. | 424/93 |
| 4,902,288 | 2/1990 | Ingram | 424/534 |
| 4,963,489 | 10/1990 | Naughton et al. | 435/1.1 |
| 5,008,116 | 4/1991 | Cahn | 424/491 |
| 5,032,508 | 7/1991 | Naughton et al. | 435/32 |
| 5,041,138 | 8/1991 | Vacanti et al. | 623/16 |
| 5,082,670 | 1/1992 | Gage et al. | 424/520 |
| 5,157,207 | 10/1992 | Carlson et al. | 935/64 |
| 5,160,490 | 11/1992 | Naughton et al. | 435/287.1 |
| 5,202,120 | 4/1993 | Silver et al. | 424/93.7 |
| 5,360,610 | 11/1994 | Tice et al. | 424/426 |
| 5,460,959 | 10/1995 | Mulligan et al. | 435/240.1 |

OTHER PUBLICATIONS

Anderson et al., "Gene expression in implanted rat hepatocytes following retroviral–mediated gene transfer," Somat. Cell Mol. Genet. 15:215–227.

Arnaout et al., 1989, "Intraperitoneal transplantation of microcarrier–attached enterocytes in rats," Am. J. Surg. 157:89–92.

Arnaout et al., 1990, "Development of bioartificial liver: Bilirubin conjugation in gunn rats," J. Surg. Res. 48:379–382.

Backlund et al., "Toward a transplantation therapy in Parkinson's disease," Ann. NY Acad. Sci. 658–673. (not dated).

Bankiewicz et al., 1987, "Transient behavioral recovery in hemiparkinsonian primates after adrenal medullary allografts," Prog. Brain Res. 78:543–549.

Bazeed et al., 1983, "New treatment for urethral strictures," Urol. XXI:53–57.

Bazeed et al., 1983, "New surgical procedure for management of peyronie disease," Urol. XXI:501–504.

Bell et al., 1981, "Living tissue formed in vitro and accepted as skin–equivalent tissue of full thickness," Science 211:1052–1054.

Bell et al., 1983, "The reconstitution of living skin," J. Invest. Dermatol. 81:2s–10s.

Breakefield, 1988, "Retroviral gene transfer of beta–nerve growth factor into cultured cells," J. Cell. Biochem., Suppl. 12 (Part B):170, Abstract H102.

Burke et al., 1984, "The effects of configuration of an artificial extracellular matrix on the development of a functional dermis," The Role of Extracellular Matrix in Development, pp. 351–355.

Buzaki et al., 1987, "Behavioral dependence of the electrical activity of intracerebrally transplanted fetal hippocampus," 400:321–333.

Chen et al., 1991, "Cellular replacement therapy for neurologic disorders: Potential of genetically engineered cells," J. Cell. Biochem. 45:252–257.

Collier et al., "Norepinephrine deficiency and behavioral senescence in aged rats," Ann. NY Acad. Sci. 396–403. (not dated).

Colombo et al., 1987, "In vitro culture and labeling of neural cell aggregates followed by transplantation," Exp. Neurol. 98:606–615.

Cowan et al., 1986, "Similar biochemical changes associated with multidrug resistance in human breast cancer cells and carcinogen–induced resistance to xenobiotics in rats," Proc. Natl. Acad. Sci. USA 83:9328–9332.

Davis et al., 1987, "Human amnion membrane serves as a substratum for growing axons in vitro and in vivo," Science 236:1106–1109.

Demetriou et al., 1986, "New method of hepatocyte transplantation and extracorporeal liver support," Ann. Surg., 204:259–271.

Demetriou et al., 1986, "Survival, organization, and function of microcarrier–attached hepatocytes transplanted in rats," Proc. Natl. Acad. Sci. USA 83:7475–7479.

Demetriou et al., 1988, "Transplantation of microcarrier–attached hepatocytes into 90% partially hepatectomized rats," Hepatol. 8:1006–1009.

Demetriou et al., 1991, "Hepatocyte transplantation: A potential treatment for liver disease," Digest. Dis. Sci. 36:1320–1326.

Faktorovich et al., 1990, "Photoreceptor rescue in the RCS rat: Effect of bFGF, aFGF and selected controls," IOVS Suppl. 31:595, Abstract. No. 2917–15.

Felcher et al., 1987, "Wound healing in normal analbuminemic (NAR) rats," J. Surg. Res. 43:546–549.

Fiandaca et al., 1988, "Adrenal medullary autografts into the basal ganglia of cebus monkeys injury–induced regeneration," Experimental Neurology 102:76–91.

Foster et al., 1988, "Transmitter expression and morphological development of embryonic medullary and mesencephalic raphe neurones after transplantation to the adult rat central nervous system," Exp. Brain Res. 70:225–241.

Freed et al., 1981, "Transplanted adrenal chromaffin cells in rat brain reduce lesion–induced rotational behavior," Nature 292:351–352.

Gage et al., 1987, "Grafting genetically modified cells to the brain: Possibilities for the future," Neuroscience 23(3):795–807.

Gage et al., 1988, "Human amnion membrane matrix as a substratum for axonal regeneration in the central nervous system," Exp. Brain Res., 72:371–380.

Gallico et al., 1984, "Permanent coverage of large burn wounds with autologous cultured human epithelium," New Eng. J. Med. 311:448–451.

Gash et al., 1986, "Amitotic neuroblastoma cells used for neural implants in monkeys," Science 233:1420–1422.

Gelderd and Quarles, 1990, "A preliminary study of homotopic fetal cortical and spinal cotransplants in adult rats," Brain Res. Bullet. 25:35–48.

Harkness et al., 1984, "Effect of pituitary hollow fiber units and thyroid supplementation on growth in the little mouse (41949)," Proc. Soc. Exp. Biol. Med. 177:312–317.

Hatton et al., 1992, "Migration of grafted rat astrocytes: Dependence on source/target organ," GLIA 5:251–258.

Hymer et al., 1981, "Pituitary hollow fiber units in vivo and in vitro," Neuroendocrinol. 32:339–349.

Hymer et al., 1981, "Pituitary hollow fiber units in the dwarf mouse," Neuroendocrinol. 32:350–354.

Hymer et al., 1987, "Heterotransplantation of human prostatic tissue," The Prostate 10:95–114.

Jaeger et L., 1988, "Plasticity of astroglia: Evidence supporting process elongation by Stretch<" GLIA 1:31–38.

Jaeger et al., 1990, "Polymer encapsulated dopaminergic cell lines as alternative neural grafts," Prog. Brain Res. 82:41–46.

Jaeger et al., 1991, "Repair of the blood–brain barrier following implantation of polymer capsules," Brain Res. 551:163–170.

Jaksic and Burke, 1987, "The use of artificial skin" for burns, Ann. Rev. Med. 38:107–117.

Kliot et al., 1990, "Astrocyte–polymer implants promote regeneration of dorsal root fibers into the adult mammalian spinal cord," Exp. Neurol., 109:57–69.

Koller and Palsson, 1993, "Tissue engineering: Reconstituation of human hematopoiesis ex vivo," Biotech. Bioengineer. 42:909–930.

Kott et al., 1991, "Ultrastructural localization of gold particles within neural grafts labeled with gold-filled sendai viral envelopes," J. Electron Microscopy Technique 18:197–202.

Langer and Vacanti, 1993, "Tissue Engineering," Science 260:920–925.

Lefkowitz et al., 1991, "Electrical properties of axons within Probst bundles of acallosal mice and callosi that have reformed upon glial-coated polymer implants," Exp. Neurol. 113:306–314.

Leonard et al., 1988, "Evidence that the M2 membrane-spanning region lines the ion channel pore of the nicotine receptor," Science 242:1578–1581.

Li et al., 1988, "Transplantation of retinal pigment epithelial cells to immature and adult rat hosts: Short–and long–term survival characteristics," Exp. Eye Res., 47:771–785.

Li et al., 1990, "Optimum conditions for long term photoreceptor cell rescue in RCS rate: The necessity for healthy RPE transplants," IOVS Suppl. 31:595, Abstract No. 2915–13.

Liesi and Silver, 1988, "Is astrocyte laminin involved in axon guidance in the mammalian CNS?," Develop. Biol., 130:774–785.

McGee et al., 1988, "Recombinant basic fibroblast growth factor accelerates wound healing," J. Surg. Res. 45:145–153.

McKeon et al., 1991, "Reduction of neurite outgrowth in a model of glial scarring following CNS injury is correlated with the expression of inhibitory molecules on reactive astrocytes," J. Neurosci., 11:3398–3411.

Montgomery and Robson, 1990, "New method of transplanting purified glial cells into the brain," J. Neurosci. Methods 32:135–141.

Montgomery and Robson, 1993, "Implants of cultured Schwann cells support axonal growth in the central nervous system of adult rats," Exp. Neurol. 122:107–124.

Moscioni et al., 1989, "Human liver cell transplantation," Gastroenterol. 96:1546–1551.

Mounzer et al., 1986, "Polyglycolic acid mesh in repair of renal injury," Urol. XXVIII:127–130.

Naughton et al., "Long–term growth of rat bone marrow cells in a three–dimensional matrix," Abstracts–AAA 100th Meeting:97A. (not dated).

Neuzil et al., 1993, "Fibroblast transplantation in rats: Transduction and function of foreign genes," J. Surg. Res. 54:631–637.

Neuzil et al., 1993, "Use of novel bioartificial liver in a patient with acute liver insufficiency," Surgery 113:340–343.

Plunkett et al., 1989, "Implantation of dispersed cells into primate brain," J. Neurosurg., 70:441–445.

Lui et al., 1990, "Propagation of adult and fetal human RPE cells for in vitro studies of growth factors and pharmacologic agents," Int. Soc. Eye Res. 6:172, Abstract No. 8.

Ptasinska–Urbanska et al., 1977, "Intrascleral introduction of isolated allogenic chondrocytes capable of cartilage reformation in rabbits; Possible procedure in treatment of detachment of the retina," Exp. Eye Res. 24:241–247.

Rosenberg et al., 1988, "Grafting genetically modified cells to the damaged brains restorative effects of NGF expression," Science 242:1575–1577.

Rozga et al., 1993, "Development of a bioartificial liver: Properties and function of a hollow–fiber module inoculated with liver cells," Hepatol. 17:258–265.

Rudge et al., 1989, "An in vitro model of wound healing in the CNS: Analysis of cell reaction and interaction at different ages," Exp. Neurol., 103:1–16.

Rudge and Silver, 1990, "Inhibition of neurite outgrowth on astroglial scars in vitro," J. Neurosci. 10:3594–3603.

Sheedle et al., 1990, "Effects of a putative RPE–cell trophic factor(s) on photoreceptor cell survival in RCS dystrophic rate," IOVS Suppl. 31:595, Abstract No. 2916–14.

Shimohama et al., 1989, "Grafting genetically modified cells into the rat brain: Characteristics of $E.$ $coli$ β–galactosidase as a reporter gene," Mol. Brain. Res., 5:271–278.

Shine et al., 1985, "Cultured peripheral nervous system cells support peripheral nerve regeneration through tubes in the absence of distal nerve stump," J. Neurosci. Res. 14:393–401.

Siegel and Langer, 1984, "Controlled release of polypeptides and other macromolecules," Pharm. Res. (1):2–10.

Silver, 1988, "Transplantation strategies using embryonic astroglial cells to promote CNS axon regeneration in neonatal and adult mammals," Clin. Res., 36:196–199.

Smith et al., 1986, "Changing role of forebrain astrocytes during development, regenerative failure, and induced regeneration upon transplantation," J. Comp. Neurol. 251:23–43.

Smith et al., 1987, "Astrocyte transplantation induces callosal regeneration in postnatal acallosal cells," Annals N.Y. Acad. Sci., 495:185–206.

Smith and Silver, 1988, "Transplantation of immature and mature astrocytes and their effect on scar formation in the lesioned central nervous system," Prog. Brain Res., 78:353–361.

Smith et al., 1990, "Maturation of astrocytes in vitro alters the extent and molecular basis of neurite outgrowth," Develop. Biol., 138:377–390.

Smith and Miller, 1991, "Immature type–1 astrocytes suppress glial scar formation, are motile and interact with blood vessels," Brain Res. 543:111–122.

Snow et al., 1990, "Sulfated proteoglycans in astroglial barriers inhibit neurite outgrowth in vitro," Exp. Neurol., 109:111–130.

Song et al., 1990, "Propagation of fetal human RPE cells: Preservation of original culture morphology after serial passage," J. Cell. Physiol., 148:196–208.

Sudhakaran et al., 1986, "Modulation of protein synthesis and secretion by substratum in primary cultures of rat hepatocytes," Exp. Cell. Res. 167:505–516.

Thilly et al., 1979, "Microcarrier culture: A homogenous environment for studies of cellular biochemistry," Methods in Enzymol., LVIII:184–187.

Thompson et al., "Implantable Bioreactors: Modern concepts of gene cultures of gene therapy," 143–147 (not dated).

Tomomura et al., 1987, "The control of DNA synthesis in primary cultures of hepatocytes from adult and young rats: Interactions of extracellular matrix components, epidermal growth factor, and the cell cycle," J. Cell. Physiol. 130:221–227.

Vacanti et al., 1988, "Selective cell transplantation using bioabsorbable artificial polymers as matrices," J. Pediat. Surg. 23:3–9.

Winn et al., 1989, "An encapsulated dopamine–releasing polymer alleviates experimental parkinsonism in rats," Exp. Neurol., 105:244–250.

Winn et al., 1989, "Brain tissue reaction to permselective polymer capsules," J. Biomed. Materials Res., 23:31–44.

Yannas and Burke, 1980, "Design of an artificial skin. I. Basic design and principles," J. Biomed. Material. Res. 14:65–81.

Yannas et al., 1982, "Wound tissue can utilize a polymeric template to synthesize a functional extension of skin," Science 215:174–176.

Yannas, 1984, "What criteria should be used for designing artificial skin replacements and how well do the currwnt grafting materials meet these criteria?," J. Trauma 24:S29–S39.

Yannas and Orgill, 1986, "Artificial skin: A fifth route to organ repair and replacement," Polymeric Biomaterials Series E:221–230.

Yannas et al., 1985, "Polymeric template facilitates regeneration of sciatic nerve across 15MM gap," Polym. Mater. Sci. Eng. 53:216–218.

Yannas et al., "Regeneration of sciatic nerve across 15mm gap by use of polymeric template," Polym. Sci. Technol. 35 (Adv. Biomed. Polym.):1–9. (not dated).

Fisher Biotech Products Catalog, pp. 72–76. (not dated).

Chen et al., J. Cellular Biochem. 45:252–257 (1991).

Rosenberg et al., Science, 242: 1575–1577 (1988).

Thilly et al., Methods in Enzymology, LVIII: 184–186 (1979).

Freed et al., Nature, vol. 292:351–352 (1981).

Demetriou et al. Replacement of Liver Function in Rats . . . Science, 12 Sep. 1986, vol. 233, pp. 1190–1192.

Illustrated Stedmen's Medical Dictionary, 24$^{th}$ ed. Baltimore: Williams & Wilkins, 1982, p. 1400.

METHOD FOR TRANSPLANTING CELLS INTO THE BRAIN AND THERAPEUTIC USES THEREFOR

CROSS-REFERENCE TO RELATED APPLICATION

The present application is a divisional application of Ser. No. 08/091,629, filed Jul. 13, 1993, now U.S. Pat. No. 5,618,531, which is a continuation of application Ser. No. 07/823,654, filed Jan. 23, 1992, now abandoned, which is a continuation-in-part of U.S. application Ser. No. 07/599,802, filed Oct. 19, 1990, now abandoned.

BACKGROUND OF THE INVENTION

1. Field of the Invention

The invention in the field of neuroscience and medicine relates to methods for implantation or transplantation of cells into the mammalian brain, useful in treating neurological disorders.

2. Description of the Background Art

The clinical management of numerous neurological disorders has been frustrated by the progressive nature of degenerative, traumatic or destructive neurological diseases and the limited efficacy and the serious side-effects of available pharmacological agents. Because many such diseases involve destruction of specific "neuronal clusters" or brain regions, it has been hoped that grafting of neural cells or neuron-like cells directly into the affected brain region might provide therapeutic benefit. Cell transplant approaches have taken on a major emphasis in current Parkinson's disease research, and may prove useful in promoting recovery from other debilitating diseases of the nervous system including Huntington's disease, Alzheimer's disease, severe seizure disorders including epilepsy, familial dysautonomia, as well as injury or trauma to the nervous system. In addition, the characterization of factors which influence neurotransmitter phenotypic expression in cells placed into the brain may lead to a better understanding of normal processes and indicate means by which birth defects resulting from aberrant phenotypic expression can be therapeutically prevented or corrected. Neurons or neuronal-like cells can be grafted into the central nervous system (CNS), in particular, into the brain, either as solid tissue blocks or as dispersed cells. However, to date, a number of problems of both a technical and ethical nature have plagued the development of clinically feasible grafting procedures.

Parkinson's disease results from a selective loss of dopaminergic nigrostriatal neurons, resulting in a loss of input from the substantia nigra to the striatum. Solid grafts of tissues potentially capable of producing dopamine, such as adult adrenal medulla and embryonic substantia nigra (SN), have been used extensively for experimental grafting in rats and primates treated with 6-hydroxydopamine (6-OHDA) to destroy dopaminergic cells (Dunnett, S. B. et al., *Brain Res.* 215: 147–161 (1981); ibid. 229: 457–470 (1981); Morisha, J. M. et al., *Exp. Neurol.* 84: 643–654 (1984); Perlow, M. J. et al., *Science* 204: 643–647, (1979)). Grafts of embryonic SN have also been used as therapy for primates lesioned with the neurotoxin 1-methyl-4-phenyl-1, 2,3,4-tetrahydropyridine (MPTP), which produces a Parkinson's -like disease (Redmond, D. E. et al., *Lancet* 8490: 1125–27 (1986)).

Stenevi et al. (*Brain Res.* 114: 1–20 (1976) found that the best results were obtained with fetal CNS neurons which were placed next to a rich vascular supply. In fact, a review of the literature reveals that tissue from almost every area of the fetal brain can be successfully transplanted if care is taken with procedural details (see, for example, Olson, L. A. et al., In: *Neural Transplants: Development and Function,* Sladek, J. R. et al., eds, Plenum Press, New York, 1984, pp. 125–165).

Embryonic tissue provides an excellent source of cells which will differentiate in a foreign environment and become integrated with the host tissue. For example, grafts of embryonic SN into 6-OHDA treated rats have been shown to produce dopamine, to reduce apomorphine- or amphetamine-induced rotation, to alleviate sensory deficits and to make synapses in the host striatum (Dunnett et al., Morisha et al., Perlow et al., supra). Grafted neurons are also spontaneously active, thus mimicking normal adult SN neurons (Wuerthele, S. M. et al., In: *Catecholamines, Part B,* (E. Usdin et al., eds.), A. R. Liss, Inc., New York, pp. 333–341).

In contrast to successful grafting of fetal neural tissue, mature CNS neurons have never been found to survive in transplants (Stenevi, U. et al., *Brain Res.* 114: 1–20 (1976)). The reason fetal CNS neurons survive grafting procedures while adult neurons do not, while uncertain, is probably related to several factors. First, fetal neurons are less affected by low oxygen levels than mature neurons (Jilek, L., In: *Developmental Neurobiology,* Himwich, W. A., ed., C. C. Thomas Publisher, Springfield, Ill., 1970, pp. 331–369), and grafting procedures necessarily involve periods of anoxia until an adequate blood supply to the transplant is established. Secondly, fetal neurons seem to survive best when they are taken during a rapid growth phase and before connections are established with target tissues (Boer, G. J. et al., *Neuroscience* 15: 1087–1109, (1985)). Also, fetal tissue may be especially responsive to growth (or "survival") factors which are known to be present in the milieu of the damaged host brain (Nieto-Sampedro, M. et al., *Science* 217: 860–861 (1982); *Proc. Natl. Acad. Sci. USA* 81: 6250–6254 (1984)).

However, despite the promise of fetal tissue and cell transplants, the art has turned to alternate sources of donor tissues for transplantation because of the ethical, moral, and legal problems attendant to utilizing fetal tissue in human medicine. These sources include neural and paraneural cells from organ donors and cultured cell lines. (See, for example: Gash, D. M. et al., In: *Neural Grafting in the Mammalian CNS,* Bjorklund, A. et al., eds, Elsevier, Amsterdam, 1985, pp. 595–603; Gash, D. M. et al., *Science* 233: 1420–22 (1986)).

Although early clinical experiments using the grafting approach did not result in long-lasting effects, an initial report of one study appeared more promising (Madrazo et al., *Soc. Neurosci. Abstr.* 12: 563 (1986); for an overview, see: Lieberman, A. et al., *Adv. Tech. Stand. Neurosurg.* 17: 65–76 (1990), which is hereby incorporated by reference). However, the surgical procedure used required craniotomy or full "open brain" surgery in which a portion of healthy striatum was removed and replaced with "chunks" of fetal adrenal gland. The therapeutic results obtained were somewhat controversial. However, both the need for serious neurosurgery in an already debilitated population and the need to use fetal tissue makes this approach undesirable.

In further human studies (Lieberman, supra; Lindvall, O., *J. Neurol. Neurosurg. Psychiat.,* 1989, Special Supplement, pp. 39–54; Bakay, R. A. E., *Neurosurg. Clin. N. Amer.* 1: 881–895 (1990)), autologous grafts have been attempted to replace the need for fetal material. In this procedure the patients first underwent initial abdominal surgery for the removal of a healthy adrenal gland. The patient then was subjected to similar neurosurgery as that for the fetal adrenal transplant. The surgical morbidity-mortality for the combined adrenalectomy/neurosurgery was expectedly high. The ultimate therapeutic result was claimed to be as high as 30% but may have been as low as one patient in the series of six. There was no evidence that the adrenal material transplanted into these patients survived.

Several additional observations suggest that grafting adrenal cells should be a viable approach. Adrenal medullary cells are derived from the neural crest and, like sympathetic neurons, grow processes in vivo or in vitro in response to nerve growth factor (NGF) (Unsicker, K. et al., *Proc. Natl. Acad. Sci. USA* 75: 3498–3502 (1978)). Solid grafts of adrenal medulla from young rats can survive in the brain of 6-OHDA treated rats for at least 5 months, produce dopamine and reduce apomorphine induced rotation (Dunnett et al., supra; Freed, W. J. et al., *Ann. Neurol.* 8: 510–519 (1980); Freed, W. J. et al. *Science* 222: 937–939 (1983)). These observations suggest that given the appropriate environment, adrenal medullary cells have the potential for growing catecholamine-synthesizing fibers into brain tissue.

The potential for neuronal differentiation of chromaffin cells is even better elucidated by grafts of dissociated adrenal chromaffin cells which grow processes when injected into rat striatum. Cultured adrenal medullary cells also differentiate into neuronal-like cells with processes when cultured in the presence of NGF (Unsicker, supra). This remarkable plasticity of adrenal cells is observed not only in morphology, but also in neurotransmitter phenotypic expression. An array of neuropeptides including vasoactive intestinal peptide, as well as the monoamine, serotonin, are co-localized with catecholamines in adrenal medullary cells (Schultzberg, M. *Neurosci.* 3: 1169–1186 (1978); Lundberg, J. M. *Proc. Natl. Acad. Sci. USA* 76: 4079–4082 (1979)). Expression of these various phenotypes can be modulated by extrinsic signals. For example, enkephalin and VIP expression are increased following denervation of the adrenal in vivo, by treatment of animals with nicotinic blockers or after maintaining adrenal cells in vitro (Tischler, A. S. *Life Sci.* 37: 1881–1886 (1985)). These observations taken together with those of other studies demonstrating that neurons derived from the neural crest can switch phenotype during normal development (Bohn, M. C. et al., *Devel. Biol.* 82: 1–10 (1981); Jonakait, G. M. et al. *Devel. Biol.* 88: 288–296 (1981)) or following experimental manipulation of the micromilieu (LeDouarin, N. M. *Science* 231: 1515–1522 (1986)) suggest that, in the future, it may be possible to control the neurotransmitter phenotype expressed by grafted cells either before and/or after grafting.

An additional advantage of grafting dissociated cells compared to blocks of tissue is that the cells can be precultured with various substances such as growth factors prior to grafting or they can be co-grafted with other cells or substances which promote specific parameters of differentiation. Furthermore, glial cells may have specific regional effects and produce neuronal growth factors (Barbin, G. et al., *Devel. Neurosci.* 7: 296–307 (1985); Schurch-Rathgeb, Y. et al., *Nature* 273: 308–309 (1978); Unsicker, K. et al. *Proc. Natl. Acad. Sci. USA* 81: 2242–2246 (1984); Whitaker-Azmitia, P. M. et al., *Brain Res.* 497: 80–85 (1989)). This suggests that co-transplanting cells providing the desired neurotransmitters along with specific types of glia which produce glial-derived factors, may promote neuronal growth and the desired differentiation of grafted cells.

The lack of success in treatment of Parkinson's Disease by transplantation of adult cells into the brain may be due in large part to the failure, for unknown reasons, of transplanted cells to thrive when placed into the brain. It is generally known (and also seen in unpublished studies by the present inventor) that cells directly injected into the brain die within about a two to four week period (see, for example, Itakura, T. et al., *J. Neurosurg.* 68: 955–959 (1988)). Despite the potential promise of using growth factors, as discussed above, actual attempts to use growth factors to prolong the transplanted cells' survival have met with extremely limited success. There is an additional, undesired, complication in the use of neuronal growth factors with chromaffin cells. Such factors often act to "transform" the chromaffin cells from a more endocrine phenotype into a neuronal phenotype, wherein total secretion of dopamine is much lower. Because of the extremely low probability of these transplanted cells establishing proper synaptic connections in the brain, the factor-induced neuronal transformation will ultimately result in cells incapable of secreting sufficient quantities of dopamine.

Thus, while the feasibility of the transplant approach has been established experimentally, this approach is severely limited by the need for the use of fetal tissue, which is of limited availability and of great political consequence. In essence, transplantation of human fetal tissue from aborted pregnancies has been prohibited in the United States. It would thus be of great benefit if simple, routine and safe methods for the successful transplantation of adult tissue into the brain were available for the treatment of debilitating neurological disease.

One potential approach to this problem has been attempted by Aebischer and his colleagues, who have successfully implanted into the brain selectively permeable biocompatible polymer capsules encapsulating fragments of neural tissue which appeared to survive in this environment (Aebischer, P. et al., *Brain Res.* 448: 364–368 (1988); Winn, S. R. et al., *J. Biomed Mater Res.* 23: 31–44 (1989). The polymer capsules, consisting of a permselective polyvinyl chloride acrylic copolymer XM-50, completely prevented the invasion of the encapsulated tissue by host cells. Based on the permeability, antibodies and viruses would be expected to be excluded as well. When dopamine-releasing polymer rods were encapsulated into such a permselective polymer and implanted into denervated striatum in rats, alleviation of experimentally-induced Parkinson disease symptoms was achieved (Winn S. R. et al., *Exp. Neurol.* 105: 244–50 (1989). Furthermore, U.S. Pat. No. 4,892,538 (Aebischer et al., issued Jan. 9, 1990) discloses a cell culture device for implantation in a subject for delivery of a neurotransmitter comprising secreting cells within a semipermeable membrane which permits diffusion of the neurotransmitter while excluding viruses, antibodies and other detrimental agents present in the external environment. The semipermeable membrane is of an acrylic copolymer, polyvinylidene fluoride, polyurethane, polyalginate, cellulose acetal, polysulphone, polyvinyl alcohol, polyacrylonitrile, or their derivatives or mixtures and permits diffusion of solute of up to 50 kD molecular weight. This device was said to be useful in treatment of neurotransmitter-deficient conditions, such as Parkinson's disease, by sustained, local delivery of neurotransmitters, precursors, agonists, fragments, etc., to a target area, especially the brain. The device may be made retrievable so that the contents may be renewed or supplemented, and the cells are protected against immunological response and viral infection.

SUMMARY OF THE INVENTION

The inventors have made the unexpected discovery that by first culturing cells in vitro on a support matrix, such as 90 μm diameter glass beads, such cells including mature CNS neurons or cultured cells, can be successfully transplanted into the mammalian brain. The beads, to which the cells adhere, are stereotaxically injected with a syringe into the recipient's brain. Cells so injected retain their viability and are thus effectively transplanted. They show prolonged survival and viability in vivo, even when transplanted across species barriers.

Adult adrenal chromaffin cells which secrete dopamine, when transplanted in this manner, are able to correct a deficit in dopamine in a rat model of Parkinson's disease. These results indicate that, not only do these cells survive for prolonged periods, but they continue to function and have therapeutic efficacy.

It is an objective of the present invention to overcome the aforementioned deficiencies in the prior work.

The present invention provides a method for grafting a cell in the brain of a mammalian subject comprising allowing the cell to attach to the surface of a support matrix in vitro, preferably by culturing the cell with the matrix, such that the cell is not encapsulated by the matrix, and implanting the support matrix with the attached cell into the brain.

The method includes support matrices made of glass or other silicon oxides, polystyrene, polypropylene, polyethylene, polyacrylamide, polycarbonate, polypentene, acrylonitrile polymer, nylon, amylases, gelatin, collagen, natural or modified polysaccharides, including dextrans and celluloses (e.g. nitrocellulose), hyaluronic acid, extracellular matrix, agar, or magnetite. Preferred support matrices are beads, porous or nonporous, in particular microbeads having a diameter from about 90 to about 150 μm.

The method of the present invention may employ cells of many different types, preferably either cells of neural or paraneural origin, such as adrenal chromaffin cells. Also useful are cell lines grown in vitro. Cells not of neural or paraneural origin, such as fibroblasts, may also be used following transfection with DNA encoding a neuropeptide or an enzyme or set of enzymes which results in production of neurotransmitter, or a neuronal growth factor.

The present invention includes a method for treating a neurological disease in a subject which comprises grafting an effective number of cells capable of treating the disease according to the above methods. Diseases which can be treated according to the present invention include, but are not limited to, Parkinson's disease, Alzheimer's disease, Huntington's disease, epilepsy, familial dysautonomia, and traumatic brain injury.

DESCRIPTION OF THE PREFERRED EMBODIMENTS

Figure 1:
FIG. 1 is a photomicrograph of a section of the brain of a rat implanted with adult adrenomedullary cells on a glass microbead. The section was fixed an stained histochemically for tyrosine hydroxylase (TH) using horse radish peroxidase. The darkly stained areas indicate cells containing TH. The pattern of staining shows a needle tract entering the section on the right side. The large circular stained area in the center represents the bulk of the implanted cells. The injected cells form a "gland-like" pattern, with some extending back into the needle tract. (Thickness: 20 microns; magnification: 100×).

The present invention is based on the unexpected discovery by the inventors that adult cells or cultured cells which cannot normally be transplanted into a mammalian brain and survive, can be made to survive by first attaching them to a support matrix.

A number of different cell types are useful for the present invention. Typically, a cell will be selected based on its ability to provide a missing substance to the recipient brain. Missing substances can be neurotransmitters or other neurally-active molecules, the absence of which results in neurological disease or dysfunction. It is important that the transplanted cell not grow as a tumor once it is inserted into the recipient.

The references cited below are all incorporated by reference herein, whether specifically incorporated or not.

By the term "neural or paraneural origin" is intended a cell which is derived from the embryonic neural crest. A preferred example of a cell of paraneural origin is a adrenal medullary chromaffin cell. The precursor cells to the mammalian adrenal medulla are of neural crest origin and possess the potential to develop along either neuronal or endocrine lines of differentiation (Bohn, M. C. et al., 1981, supra, *Devel. Biol.* 89: 299–308 (1982); Unsicker, K., *Develop. Biol.* 108: 259–268 (1985)). Chromaffin cells from the rat, monkey, and human adrenal medulla, when removed from adrenal cortical influences and exposed to nerve growth factor (NGF), change from an endocrine to a neuronal phenotype (Notter, M. F. et al., *Cell Tiss. Res.* 244: 69–70 (1986); Stromberg, I. et al., *Exp. Brain Res.* 60: 335–349 (1985); Unsicker, K. et al., 1978, supra). When co-grafted with cerebral cortical or hippocampal tissue into the anterior chamber of the rat eye, adrenal chromaffin cells form nerve fibers which innervate the adjacent co-grafted brain tissue (Olson, L. A. et al., *Exp. Neurol.* 70414–426 (1980)). Another paraneural cell type is a retinal pigment epithelium cell (Song, M-K et al., *J. Cell. Physiol.* 148: 196–203 (1990)).

One source of donor cells are established neural cell lines. Many neuronal clones exist which have been used extensively as model systems of development since they are electrically active with appropriate surface receptors, specific neurotransmitters, synapse forming properties and the ability to differentiate morphologically and biochemically into normal neurons. Neural lines may express a tremendous amount of genetic information which corresponds to the genetic expression seen in CNS neurons. Such cells are described in the following references: Kimhi, Y. et al., *Proc. Natl. Acad. Sci. USA* 73: 462–466 (1976); In: *Excitable Cells in Tissue Culture*, Nelson, P. G. et al., eds., Plenum Press, New York, 1977, pp. 173–245); Prasad, K. M. et al., In: *Control of Proliferation of Animal Cells*, Clarkson, B. et al., eds., Cold Spring Harbor Laboratory Press, Cold Spring Harbor, N.Y., 1974, pp. 581–594); Puro, D. G. et al., *Proc. Natl. Acad. Sci. USA* 73: 3544–3548 (1976); Notter, M. F. et al., *Devel. Brain Res.* 26: 59–68 (1986); Schubert, D. et al., *Proc. Natl. Acad. Sci. USA* 67: 247–254 (1970); Kaplan, B. B. et al., In: *Basic and Clinical Aspects of Molecular Neurobiology*, Guffrida-Stella, A. M. et al., eds., Milano Fondozione International Manarini, 1982)).

A major advantage of these cultured cells has been the potential to manipulate the environment, as well as the cells themselves, in controlling the phenotype and genotype.

For example, human neuroblastoma cells from the IMR 32 cell line can survive and express cholinergic markers in primate brain nine months after transplantation (Gash, D. M. et al., *Science* 233: 1420–22 (1986)). These cells are preferably treated to render them morphologically and biochemically differentiated in vitro and must be rendered permanently amitotic before implantation, which further aids in their survival (Gash et al., supra; Gupta, M. et al., *Dev. Brain Res.* 19: 21–29 (1985)).

Whereas untreated pheochromocytoma/neuroblastoma cells (PC12 cells) which grafted into the adult rat striatum showed no survival after two weeks in vivo (Hefti, F. et al., *Brain Res.* 348: 283–288 (1985)), treatment in vitro with NGF to stimulate neural cell differentiation followed by exposure to antimitotic agents to inhibit cell proliferation, does not deleteriously affect catecholamine neurotransmitter expression nor viability and is of value for stimulating performance following transplant. Therefore, in one embodiment of the present invention, cell line cells are modulated in vitro with the appropriate growth or differentiation factor and with an amitotic agent before transplantation in order to promote cell survival and prevent expression of the malignant potential.

It will be apparent to one of ordinary skill in the art that examination of the neural cell surface of clonal cells in vitro using conventional methods will permit the selection of appropriate cells for use according to the present invention. During normal development and differentiation, the neuronal cell surface undergoes significant changes which account for the migration, recognition and integration of neurons in the CNS. For example, when mouse C1300 clonal, neural cell lines are treated with antimitotic agents or growth modulators such as prostaglandin $E_1$ and cyclic AMP, new low molecular weight cell surface glycoproteins are produced (Bottenstein, J. E., In: *Functionally Differentiated Cell Lines*, Sato, G. H., ed., Alan R. Liss, New York, 1981). CNS surface gangliosides are induced which bind tetanus toxin (Notter, M. F., 1986, supra) while specific lectin binding glycoproteins appear which are similar to normal central nervous system glycoproteins. Additionally, receptors for neurotransmitters and neuropeptides on neuroblastoma cells can be modified in a manner similar to cells found in the CNS (Costa, L. G. et al., *Biochem. Pharmacol.* 91: 3407–3413 (1982).

Another important source of potential graft material are cells engineered by somatic cell hybridization, a process which can immortalize single neurons. Somatic cell hybridization is a powerful cell biologic tool used not only to generate cell lines with a variety of genotypes but to analyze the mechanisms regulating the expression of various phenotypes of differentiation. Fusing cells which differ in the expression of specific genes allows for the exploration of the mechanisms controlling gene expression while chromosome alterations occur at rates to generate genetically different cell lines. Hybrid cells can be formed which retain the properties of differentiated cells. Hybrids derived from fusion of sympathetic ganglia and neuroblastoma cells can synthesize dopamine (Greene, L. A. et al., *Proc. Natl. Acad. Sci. USA* 82: 4923–4927 (1975) while brain cell hybrids express choline acetyltransferase (Minna, J. D. et al., *Genetics* 79: 373–383 (1975)). Therefore, embryonic precursors to dopaminergic neurons from the CNS can be fused with mitotic cells to incorporate both genomes into a single one that loses extra chromosomes over time and results in a new hybrid line. It is within the skill of the art to produce such hybrid neural or paraneural cells without undue experimentation, screen them for the desired traits, such as dopamine secretion, and select those having the best potential for transplantation.

Another source of cells for transplantation according to the present invention is the adrenal medulla. This neural crest-derived tissue has been involved in clinical trials (see Background) to treat Parkinson's disease. Adult monkey adrenal medulla can be cultured in vitro for at least about three weeks as single cells (Notter, M. F. et al., *Cell Tiss. Res.* 244: 69–76 (1986)). These cells respond to NGF by phenotypic alteration from the epithelioid, glandular morphology, to a neuronal morphology in which cells show extensive neuritic arborizations containing microtubular arrays. This neuronal phenotype appears to be critical for long term survival of rat medullary cells in host CNS as well as their integration with host tissue (Stromberg, L. et al., supra). Transplanted adrenal medulla tissue can correct functional deficits resulting from nigrostriatal dopamine depletion in rats (see, for example, Freed et al., 1981, supra). This, however, is thought to be brought about by diffusion of dopamine from the transplant, a phenomenon that decreases three to six months after transplantation. NGF treatment of the transplanted cells induces fiber outgrowth from the transplant into the host and induces a longer lasting behavioral recovery (at least a year). Indeed, without NGF treatment, few chromaffin cells transplanted either to rat (Freed et al., supra) or rhesus monkey caudate nucleus (Morihisia, J. M. et al., *Exp. Neurol.* 84: 643–653 (1984) using prior art techniques survive.

Similarly, retinal pigment epithelial cells secrete dopamine and other factors and may be used for brain implants according to the present invention (Li, L. et al., *Exp. Eye Res.* 47: 771–785 (1988); Lui, G. M. et al., *Proc. Int'l. Soc. Eye Res.* 6: 172 (1990); Li, L. et al., *Inv. Ophthal. Vis. Sci.* 31(Suppl): 595 (1990, abstr. 2915–13); Sheedlo, H. J. et al., ibid., abstr. 2916–14; Fektorovich, E. G. et al., ibid. (abstr. 2917–15); Song, M-K et al., supra).

Cells transplanted into the mammalian brain according to the present invention have shown survival in the absence of added growth factors. However, an additional embodiment of the present invention is directed to transplantation of cells attached to a support matrix combined with the treatment, either in vitro prior to transplant, in vivo after transplant, or both, with the appropriate growth/differentiation factor.

Human adrenal medullary cells can be maintained in vitro having the neuronal phenotype for at least nine weeks (Notter, M. F. et al., *Schmitt Neurol. Sci. Symp.*, Jun. 30, 1987, abstr.). NGF induces this conversion from the glandular state. Adrenal medullary cells co-cultured with C6 glioma cells exhibit extensive neuritic arborization and intimate contact with glioma cells. These astrocytic cells, treated with antimitotic agents to inhibit mitosis, are known to produce a growth factor similar to NGF which sustains sympathetic neurons in vitro (Barde, Y. A., *Nature* 274: 818 (1978)). Grafted glial cells may play an important role in functional recovery of neurons and may be an important source of trophic factors (Doering, L. C. et al., *J. Neurolog. Sci.* 63: 183–196 (1984); Gumple, J. et al., *Neurosci. Lett.* 37: 307–311 (1984)). Therefore, another embodiment of the present invention involves co-culture of neural or paraneural cells with glial cells, their co-incubation with a support matrix, followed by implantation of the support matrix carrying both cell types.

In additional embodiments of the present invention, cells which are not of neural or paraneural origin, but which have been altered to produce a substance of neurological interest, are used. A preferred cell type is a human foreskin fibroblast which is easily obtained and cultured, and survives upon transplantation into the rat brain using the methods of the present invention (see Example III). For use in the present invention, the cells are genetically altered, using methods known in the art, to express neuronal growth factors, neurotransmitters, neuropeptides, or enzymes involved in brain metabolism. (See, for example, Gage, F. H. et al., *Neuroscience* 23: 795–807 (1987); Rosenberg, M. B. et al., *Science* 242: 1575–1578 (1988); Shimohama, S. et al., *Mol. Brain Res.* 5: 271–278 (1989); which are hereby incorporated by reference).

Standard reference works setting forth the general principles of recombinant DNA technology and cell biology, which are hereby incorporated by reference, include Watson, J. D., et al., *Molecular Biology of the Gene*, Volumes I and II, Benjamin/Cummings Publishing Co., Inc., Menlo Park, Calif. (1987); Darnell, J. E. et al., *Molecular Cell Biology*, Scientific American Books, Inc., New York, N.Y. (1986); Lewin, B. M., *Genes II*, John Wiley & Sons, New York, N.Y. (1985); Old, R. W. et al., *Principles of Gene Manipulation: An Introduction to Genetic Engineering*, 2nd Ed., University of California Press, Berkeley, Calif. (1981); Maniatis, T., et al. (*Molecular Cloning: A Laboratory Manual*, Cold Spring Harbor Press, Cold Spring Harbor, N.Y. (1982)); Sambrook, J. et al. (*Molecular Cloning: A Laboratory Manual*, 2nd Edition, Cold Spring Harbor Press, Cold Spring Harbor, N.Y. (1989) and Albers, B. et al., *Molecular Biology of the Cell*, 2nd Ed., Garland Publishing, Inc., New York, N.Y. (1989).

The recombinant DNA molecules useful for the methods of the present invention can be produced through any of a variety of means, such as, for example, DNA or RNA synthesis, or more preferably, by application of recombinant DNA techniques. Techniques for synthesizing such molecules are disclosed by, for example, Wu, R., et al. (*Prog. Nucl. Acid. Res. Molec. Biol.* 21: 101–141 (1978)). Procedures for constructing recombinant molecules are disclosed in detail by Sambrook et al., supra).

Typically, the gene or genes of interest are cloned from a library of expression vectors which has been prepared by cloning DNA or, more preferably, cDNA (from a cell capable of expressing the gene) into an expression vector. The library is then screened for members capable of expressing the gene product of interest, such as a neurotransmitter-synthesizing enzyme, using antibody binding with an antibody specific for the gene product. DNA, or more preferably cDNA, is extracted and purified from a cell which is capable of expressing the gene product of interest. The purified cDNA is fragmentized (by shearing, endonuclease digestion, etc.) to produce a pool of DNA or cDNA fragments. DNA or cDNA fragments from this pool are then cloned into an expression vector in order to produce a library of expression vectors whose members each contain a unique cloned DNA or cDNA fragment.

An "expression vector" is a vector which (due to the presence of appropriate transcriptional and/or translational control sequences) is capable of expressing a DNA (or cDNA) molecule which has been cloned into the vector and of thereby producing a polypeptide or protein. Expression of the cloned sequences occurs when the expression vector is introduced into an appropriate host cell. An appropriate mammalian host cell would be any mammalian cell capable of expressing the cloned sequences. Procedures for preparing cDNA and for producing a genomic library are disclosed by Sambrook et al. (supra).

A DNA sequence encoding a product or products the expression of which is desired for the present invention may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Sambrook et al., supra, and are well known in the art.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression. The precise nature of the regulatory regions needed for gene expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. Such regions will normally include those 5'-non-coding sequences involved with initiation of transcription and translation, such as the TATA box, capping sequence, CAAT sequence, and the like.

If desired, the non-coding region 3' to the gene sequence coding for the protein may be obtained by the above-described methods. This region may be retained for its transcriptional termination regulatory sequences, such as termination and polyadenylation. Thus, by retaining the 3'-region naturally contiguous to the DNA sequence coding for the protein, the transcriptional termination signals may be provided. Where the transcriptional termination signals are not satisfactorily functional in the expression host cell, then a 3' region functional in the host cell may be substituted.

Two DNA sequences (such as a promoter region sequence and a coding sequence) are said to be operably linked if the nature of the linkage between the two DNA sequences does not (1) result in the introduction of a frame-shift mutation, (2) interfere with the ability of the promoter region sequence to direct the transcription of the coding sequence, or (3) interfere with the ability of the coding sequence to be transcribed by the promoter region sequence. A promoter region would be operably linked to a DNA sequence if the promoter were capable of effecting transcription of that DNA sequence. Thus, to express the protein, transcriptional and translational signals recognized by the host cell are necessary.

A promoter is a double-stranded DNA or RNA molecule which is capable of binding RNA polymerase and promoting the transcription of an "operably linked" nucleic acid sequence. As used herein, a "promoter sequence" is the sequence of the promoter which is found on that strand of the DNA or RNA which is transcribed by the RNA polymerase. A "promoter sequence complement" is a nucleic acid molecule whose sequence is the complement of a "promoter sequence." Hence, upon extension of a primer DNA or RNA adjacent to a single-stranded "promoter sequence complement" or, of a "promoter sequence," a double-stranded molecule is created which will contain a functional promoter, if that extension proceeds towards the "promoter sequence" or the "promoter sequence complement." This functional promoter will direct the transcription of a nucleic acid molecule which is operably linked to that strand of the double-stranded molecule which contains the "promoter sequence" (and not that strand of the molecule which contains the "promoter sequence complement").

The promoter sequences useful for producing cells for the present invention may be either eukaryotic or viral. Suitable promoters are repressible, or, more preferably, constitutive. Useful eukaryotic promoters include the promoter of the mouse metallothionein I gene (Hamer, D., et al., *J. Mol. Appl. Gen.* 1: 273–288 (1982)); the TK promoter of Herpes virus (McKnight, S., *Cell* 31: 355–365 (1982)); the SV40 early promoter (Benoist, C., et al., *Nature* (London) 290: 304–310 (1981)). A preferred promoter, in particular for human fibroblasts, is the collagen promoter (Prockop, D. J. et al., *N. Eng. J. Med.* 301: 13–23, 77–85 (1979); Eyre, D. R., *Science* 207: 1315–1322 (1980); Martin, G. R. et al., *Trends Bioch. Sci.* 10: 285–287 (1985); which references are hereby incorporated by reference).

Also intended within the scope of the present invention are cells attached to, or mixed with, a support matrix, according to the invention, which are frozen and stored in a frozen state using methods well known in the art. Following thawing, the matrix-bound cells are implanted into a recipient brain.

The cells useful in the methods of the present invention may be xenogeneic (=heterologous, i.e., derived from a species different from the recipient), allogeneic (=homologous, i.e., derived from a genetically different member of the same species as the recipient) or autologous, wherein the recipient also serves as the donor.

The number of cells needed to achieve the purposes of the present invention is variable depending on the size, age, weight of the subject, the nature of the underlying disease, other concurrent therapies, and the like. This can be determined by one of skill in the art without undue experimentation. In an adult human, an effective number of cells attached to a support matrix are in the range of about $1 \times 10^3$ to about $1 \times 10^7$ cells, more preferably about $5 \times 10^3$ to about $1 \times 10^6$ cells. Alternatively, the effective amount of transplanted cells can be determined in terms of mass of cells added to a volume of beads, for example 40 mg of cell mass per ml of beads.

Materials of which the support matrix can be comprised include those materials to which cells adhere following in vitro incubation, and on which cells can grow, and which can be implanted into a mammalian brain without producing a toxic reaction, or an inflammatory or gliosis reaction which would destroy the implanted cells or otherwise interfere with their biological or therapeutic activity. Such materials may be synthetic or natural chemical substances or substances having a biological origin. The matrix-materials include, but are not limited to, glass and other silicon oxides, polystyrene, polypropylene, polyethylene, polyvinylidene fluoride, polyurethane, polyalginate, polysulphone, polyvinyl alcohol, acrylonitrile polymers, polyacrylamide, polycarbonate, polypentene, nylon, amylases, gelatin, collagen, natural and modified polysaccharides, including dextrans and celluloses (e.g. nitrocellulose), agar, and magnetite. Either resorbable or non-resorbable materials may be used. Also intended are extracellular matrix materials, which are well-known in the art (see below). Extracellular matrix materials may be obtained commercially or prepared by growing cells which secrete such a matrix, removing the secreting cells, and allowing the cells which are to be transplanted to interact with and adhere to the matrix.

The support matrix of the present invention is distinguished from that described by Aebischer and his colleagues (see above) in that, according to the present invention, the cells are attached to or coating the surface of the support; they are not encapsulated within a closed compartment, where their survival would be questionable given the exclusion capacity of the disclosed encapsulating supports. Furthermore, the support matrix of the present invention presents no requirement that the material have particular permeability properties, such as the selective permeability of the Aebischer devices which allow low molecular weight substances to cross but exclude larger molecules (>50 kD).

When attached to the support according to the present invention, the cells used for transplantation are generally on the "outer surface" of the support. The support may be solid or porous. However, even in a porous support, the cells are in direct contact with the external milieu without an intervening membrane or other barrier. Thus, according to the present invention, the cells are considered to be on the "outer surface" of the support even though the surface to which they adhere may be in the form of internal folds or convolutions of the porous support material which are not at the exterior of the particle or bead itself.

The configuration of the support is preferably spherical, as in a bead, but may be cylindrical, elliptical, a flat sheet or strip, a needle or pin shape, and the like. A preferred form of support matrix is a glass bead. Another preferred bead is a polystyrene bead. Bead sizes may range from about 10 μm to 1 cm in diameter, preferably from about 90 to about 150 μm. For a description of various microcarrier beads, see, for example, *Fisher Biotech Source* 87–88, Fisher Scientific Co., 1987, pp. 72–75; *Sigma Cell Culture Catalog*, Sigma Chemical Co., St. Louis, 1991, pp. 162–163; *Ventrex Product Catalog*, Ventrex Laboratories, 1989; these references are hereby incorporated by reference. The upper limit on the bead size is dictated by the bead's stimulation of undesired host reactions such as gliosis, which may interfere with the function of the transplanted cells or cause damage to the surrounding brain tissue. Such limitations are readily determinable by one of skill in the art.

To improve cell adhesion, survival and function, the solid matrix may optionally be coated on its external surface with factors known in the art to promote cell adhesion, growth or survival. Such factors include cell adhesion molecules, extracellular matrix, such as, for example, fibronectin, laminin, collagen, elastin, glycosaminoglycans, or proteoglycans (see: Albers, B. supra, pp. 802–834) or growth factors, such as, for example, NGF. Alternatively, if the solid matrix to which the implanted cells are attached is constructed of porous material, the growth- or survival-promoting factor or factors may be incorporated into the matrix material, from which they would be slowly released after implantation in vivo.

In an alternate embodiment of the present invention, cells growing on, or mixed with, resorbable matrices, such as, for example, collagen, can be implanted in sites of neurological interest other than the brain, in order to promote neuronal regrowth or recovery. For example, cells attached to the matrix of the invention may be implanted into the spinal cord, or placed in, or adjacent to, the optic nerve.

The matrix material on which the cells to be implanted grow, or with which the cells are mixed, may be an endogenous product of the implanted cells themselves. Thus, for example, the matrix material may be extracellular matrix or basement membrane material which is produced and secreted by the very cells to be implanted.

The methods of the present invention are useful for treating a number of human neurological disease. Parkinson's Disease can be treated according to the present invention by implanting dopamine-producing cells in the recipient's striatum. Alzheimer's disease involves a deficit in cholinergic cells in the nucleus basalis. Thus, according to the invention, a subject having Alzheimer's disease or at risk therefor may be implanted with cells producing acetylcholine.

Huntington's disease involves a gross wasting of the head of the caudate nucleus and putamen, usually accompanied by moderate disease of the gyrus. A subject suffering from Huntington's disease can be treated by implanting cells producing the neurotransmitters gamma amino butyric acid (GABA), acetylcholine, or a mixture thereof. According to the present invention, the support matrix material to which such cells are attached is preferably implanted into the caudate and putamen.

Epilepsy is not truly a single disease but rather is a symptom produced by an underlying abnormality. One skilled in the art will appreciate that each epileptic subject will have damage or epileptic foci which are unique for the individual. Such foci can be localized using a combination of diagnostic methods well-known in the art, including electroencephalography, computerized axial tomography and magnetic resonance imaging. A patient suffering from epilepsy can be treated according to the present invention by implanting the support matrix material to which GABA-producing cells are attached into the affected site. Since blockers of glutamate receptors and NMDA receptors in the brain have been used to control experimental epilepsy, cells producing molecules which block excitatory amino acid pathways may be used according to the invention. Thus implantation of cells which have been modified as described herein to produce polyamines, such as spermidine, in larger than normal quantities may be useful for treating epilepsy.

The methods of the present invention are intended for use with any mammal which may experience the beneficial effects of the methods of the invention. Foremost among such mammals are humans, although the invention is not intended to be so limited, and is also applicable to veterinary uses.

Having now generally described the invention, the same will be more readily understood through reference to the following examples which are provided by way of illustration, and are not intended to be limiting of the present invention, unless specified.

EXAMPLE I

Adrenal chromaffin cells from adult rats were prepared according to known methods (see Example IV, below; see also, Inoue, M. et al., *A. J. Physiol.* 257 (Cell Physiol.) :C906–912 (1989)). After sacrifice by nembutal anesthesia followed by decapitation adrenal glands were removed. The medulla was freed of capsular and cortical material by careful microdissection. The tissue was cut into 2 or 3 pieces and incubated for 30 minutes with 0.2% collagenase in calcium-free balanced salt solution containing 140 mM NaCl, 5 mM KCl, 5.2 mM $MgCl_2$, 5 mM HEPES, 10 mM D-glucose, at pH 7.4. During the enzyme treatment, the preparation was shaken gently by bubbling through 99.9% $O_2$. After digestion, the tissue was washed three or four times with the above salt solution and then triturated gently in a pasteur pipet.

The dissociated chromaffin cells were transferred to cell culture flasks containing serum free medium (Ventrex PC 1) and were cultured overnight at 37° C. in a 5% $CO_2$ atmosphere. Under these conditions, the cells retain their viability for no more than a few days. Sterilized glass beads (Ventrex, 90 micron) were added to the culture flask. The cells attached to the beads and essentially formed a monolayer on the beads.

Within 24 hrs. of preparation in vitro, 1 to 5 µl aliquots of the cell-carrying bead suspension were injected into the brains of anesthetized adult rats. Later analysis, at times when the cells would not have survived in culture, the cells were found to be viable in vivo in the site surrounding the injection, (see FIG. 1) as determined by immunocytochemical staining for tyrosine hydroxylase according to the Weiner procedure (see: Kilpatrick, D. L. et al., *J. Neurochem.* 35: 679 (1980); Hokfelt, R. et al., *Handbook of CHemical Neuroanatomy*, Elsevier Science Publishers, Amsterdam, 1985). The glass beads produced no necrotic damage above that typical of the injection itself.

EXAMPLE II

Adrenal medullae were removed from adult guinea pigs according to methods described in Examples I and IV and subjected to the procedure described in Example I. The cells on glass microbeads were injected into rat brain. The cells survived for a period of at least 21 days in a completely healthy state. No signs of immunological rejection were evident.

EXAMPLE III

Cultured human foreskin fibroblasts were attached to glass microbeads as described above and injected into the rat brain. The cells were localized by immunofluorescence using human IgG which selectively bound to the fibroblasts, followed by a fluorescein-conjugated goat anti-human IgG antibody. The implanted human cells survived for a period of at least 21 days in a completely healthy state. No signs of immunological rejection were evident.

EXAMPLE IV

Adrenal Chromaffin Cells Transplanted on Microcarriers Correct a Lesion of Nigrostriatal Dopaminergic Cells Studies were conducted to test the ability of adrenal chromaffin cells attached to microcarriers, shown above to survive for prolonged periods in the brain, to carry out a physiological function, i.e. dopamine secretion, and correct a lesion in the dopamine system.

A standard animal model for Parkinson's disease was used. Nigrostriatal dopaminergic neurons are destroyed locally and selectively by stereotaxic injection of 6-OHDA. Subsequent injection of apomorphine, a dopaminergic agonist, induces rotational or turning behavior in lesioned but not in normal rats. Therapy of the Parkinson-like symptoms is assessed by a decrease in this turning behavior.

Animals

Male Sprague-Dawley rats, obtained from Tacona at a weight of 120–150 grams, were maintained in the Berg Institute at NYU Medical Center, an approved animal facility, and were provided with food and water ad libitum. Animals were lesioned when they had attained a weight of 180 to 200 grams.

Destruction of Substantia Nigra (SN)

A lesion was induced in the SN by stereotaxic application of the selective neurotoxic agent, 6-OHDA. Rats were anesthetized using sodium pentobarbital, 45 mg/kg, i.p. Animals were placed in a Kopf-type stereotaxic instrument. For lesioning the right side, the following coordinates were used: Rostral Caudal: −4.8 mm; Dorsal Ventral: −8.1 mm; Lateral Medial: −1., −2.0 mm; Jaw Bar: −3.3 mm.

After the induction of Nembutal anesthesia, the rat's head was shaved using an Oster clipper with surgical blade. The rat was then placed into the stereotaxic apparatus and its head approximately positioned. A ¾ inch rostral-caudal incision was made midline in the cranium. The skull was gently scraped using a #10 scalpel blade to remove the pericranial membranes. The bregma was located and the injection needle was placed directly over this landmark. Stereotaxic coordinates were then corrected for the individual animal using the position directly over the bregma as the zero-value coordinates. For a right-side unilateral lesion of the SN, the rostral-caudal coordinate was subtracted from the zeroed value and the lateral-medial coordinate was subtracted from the zeroed value. These correction placed the needle directly above the SN.

The needle was then lowered to touch the skull and the point of contact was marked with a pencil. The needle was then raised out of the way and a hole was drilled through the cranium using a Dremel Flex-shaft drill equipped with a #253 handpiece and a #6 dental bit. The needle was repositioned above the opening in the skull and then lowered into the hole so that it sat just inside the entrance. The stereotaxic coordinate of this position was recorded as the dorsal-ventral zero value with the needle at the dura mater. The dorsal-ventral value was then subtracted from this value to give the desired final coordinate. The needle was then lowered to the corrected dorsal ventral coordinate for the injection.

The 6-OHDA hydrobromide in a vehicle of isotonic (0.9%) saline containing 0.2 mg/ml ascorbic acid was used at a concentration of 8 μg/4 μl. The agent was prepared immediately prior to injection to minimize oxidative degradation of this drug and was kept on ice until it was used. The drug was injected using a perfusion pump attached to a 23 gauge needle at a rate of 1 μl/min until a total volume of 4 μl had been injected. Prior to removal, the needle was allowed to remain in place for an additional 5 minutes to allow for infiltration of the drug into the desired area.

The surgical site was closed using Clay-Adams 9 mm wound clips, and the rats were allowed to recover. After the surgery, the animal was placed into a warm container and allowed to recover from the anesthesia prior to its return to its normal housing in Berg Institute. By the next day, the rats had regained normal behavior.

Behavioral Testing

To assess the effects of the SN lesion, animals were the apomorphine-induced rotational movement paradigm was used. Rats were injected subcutaneously with apomorphine, 0.25 mg/kg, and were observed for signs of dopamine-induced stereotypical behavior: licking, ptosis of the eyelids, gnawing, etc. The time of onset was recorded. The animal was observed for the initiation of rotational movement, and the time was recorded. Rats lesioned in their SN with 6-OHDA lesioned rat are known to exhibit tight contralateral rotations when injected with apomorphine.

Five minutes after apomorphine administration, quantitation of the rotational movement was initiated. Only complete 360° turns were recorded. Quantitation of movement continued for 25 minutes. Rats were scored on the basis of turns per minute. Rats exhibiting less than 7 apomorphine-induced turns per minute were rejected from the study. Rats were tested at weekly intervals until the rotational behavior stabilized, usually at three to four weeks post-injection, and remained stable for an additional two testing periods. In general, rats exhibited 9 to 10 apomorphine-induced turns per minute at this time, and were ready for transplant studies.

Preparation of Chromaffin Cells

Donor rats were anesthetized using sodium pentobarbital, 45 mg/kg, i.p.. After the induction of anesthesia, the rat was placed on its back in a sterile surgical field and the adrenal gland was removed under sterile conditions. An "T"-shaped incision was made for the length of the abdominal cavity and the skin flaps were pulled back. The peritoneum was then opened and the kidneys were exposed. The kidney and its associated adrenal gland was freed from the perirenal fat pad by blunt dissection. The kidney/adrenal gland was removed from the animal and placed into a culture dish containing PC-1 medium (Ventrex). The capsule was opened and the entire adrenal gland was carefully dissected free of the kidney.

The free adrenal was transferred to a 60 mm culture dish containing Ventrex PC-1 supplemented medium. The adrenal was minced as finely as possible using a scalpel. The medium was carefully decanted and replaced with 10 ml sterile complete PC-1 medium containing 0.1% Trypsin/ 0.2% collagenase. The adrenal was incubated in this solution for 30 mins. in a 37° C. incubator in an atmosphere of 5% carbon dioxide in air.

Following this incubation, the cell mixture was made homogeneous by repeatedly drawing it up and down through a sterile 10 ml plastic pipette and was then passed through a 100 μm cell sieve. The clean filtrate was placed in a sterile tube and centrifuged at 200×g for 5 min. The supernatant was decanted and the cell-containing pellet was resuspended in complete PC-1 medium, which included the "serum-like" factors. (3–4 ml if cells were to be cultured on microcarriers). The mixture was shaken gently and placed in a 37° C. incubator.

Culturing the Cells on Microcarriers

Ventrex glass microcarriers (Ventreglas, 90–120 μm) were sterilized by placing the beads in 10 ml of sterile distilled water per 1 gram of beads and heating to 121° C. for 15 min. The solution was allowed to cool to room temperature and the water was discarded. The microcarriers were then suspended into a small volume of culture medium and allowed to stand for 30 mins. The medium was removed and the beads (approximately 0.21 g) were added to the previously described cell preparation. The resulting mixture was shaken for 2 hours and an additional 4 ml of complete PC-1 was added. The culture flask was then incubated overnight at 37° C. in a 5% $CO_2$ atmosphere to allow the cells to adhere to the microcarriers.

Additional cell types which have been testing by the present inventors using this methodology include human retinal pigment epithelial cells and human foreskin fibroblasts. These cell types have been tested only for survival in the recipient animal's brain, and have given positive results in experiments lasting up to four months. (see Example I).

Transplantation of Cells

The cells were injected into caudate/putamen region of the brain using a stereotaxic injection. The Atlas coordinates used for the injection were: Rostral Caudal: −3.14; Dorsal Ventral: −7.4; Lateral Medial: −5.0; Jaw Bar: −3.3. Corrected values were derived as previously described.

In initial experiments, a 23 gauge needle was used for the injection. There was a tendency for the microcarriers to sediment during the injection and clog the needle. This problem was partially alleviated using a larger needle. However, the use of a straight bore or beveled needle resulted also in brain tissue entering the bore and plugging the needle. This was been corrected using a needle with the tip bent over to protect the opening. Using this type of needle, it has been possible to evenly inject the cells into the brain.

As a result of this modification, the stereotaxic coordinates required further correction for the actual opening of the needle rather than its tip. This was accomplished by measurement of the tip-opening distance (typically 1–2 mm) and appropriate reduction of the values given above. Once the needle was properly placed, the suspension containing microcarrier-adhering cells was injected at a rate of 4 µl/min until a final volume of 20 µl had been injected. The total number of beads injected varied somewhat due to sedimentation during the injection, but was calculated to be about 170–200 beads. Current estimates are that approximately 175 beads (each holding 2–5 cells) need to be injected to obtain an excellent therapeutic response. This number extrapolates to 50,000 to 75,000 beads in the human, occupying a volume of about 0.5 ml.

Recovery and Testing of Animals Receiving Cell Implants

After injection, the surgical site was closed using Clay-Adams 9 mm. wound clips, and the rat was allowed to recover. For the first two hours after the surgery, the animal was kept in a warmed container to recover from the anesthesia. The animal was then returned to its normal housing in Berg Institute. By the next day, the rats had regained normal behavior. No morbidity or mortality was associated with the cell implantation procedure.

Testing of animals for rotational behavior began two days after the surgery and continued at weekly intervals for one month and at monthly intervals thereafter. Rats have been tested for up to 4.5 months. Successful function of the implanted cells in secreting dopamine was measured as a reduction in the apomorphine-induced turning behavior described above in the unilaterally 6-OHDA-lesioned rats.

Histologic Analysis

Rats were anesthetized with sodium pentobarbital, 60 mg/mg i.p., the chest cavity was opened to expose the heart. A 22 gauge butterfly needle was inserted into the bottom of the left ventricle, and the right atrium was cut. The butterfly needle was attached to a peristaltic pump and isotonic saline was pumped through the heart until the solution leaving the cut atrium appeared clear. In general, 200–400 ml of saline were required. The perfusion solution was then changed to 1% glutaraldehyde/1% paraformaldehyde/0.1M sodium phosphate, pH 7.2. The perfusion was continued with this fixative until the liver achieved a whitish color. This required approximately 400 ml of perfusion fluid. After successful perfusion, the rats were stiff. The rat was removed from the perfusion apparatus and decapitated. The head was placed into a solution of 2% glutaraldehyde and allowed to soak for 2 hours. At the end of this time, the brain was removed and frozen-sectioned in a microtome at a thickness of 26 to 28 µm. Sections were transferred to numbered test-tubes containing phosphate buffered saline, pH 7.2. Sections were examined at low power under a dissecting microscope to select those for further study.

The sections were stained as appropriate and mounted on gelatin-coated slides. To gelatin-coat the microscope slides, a filtered solution containing 3 g gelatin, 0.3 g chromium potassium sulfate in 600 ml distilled water was freshly prepared and the slides were individually immersed once in this solution. The slides were allowed to dry in open air overnight. The section was then mounted on the slide and dehydrated by immersing for 5 minutes each in 70% alcohol, 90% alcohol, 95% alcohol, twice in 100% alcohol and twice in xylene. Coverslips were then mounted using Permount solution.

RESULTS

Figure 2:
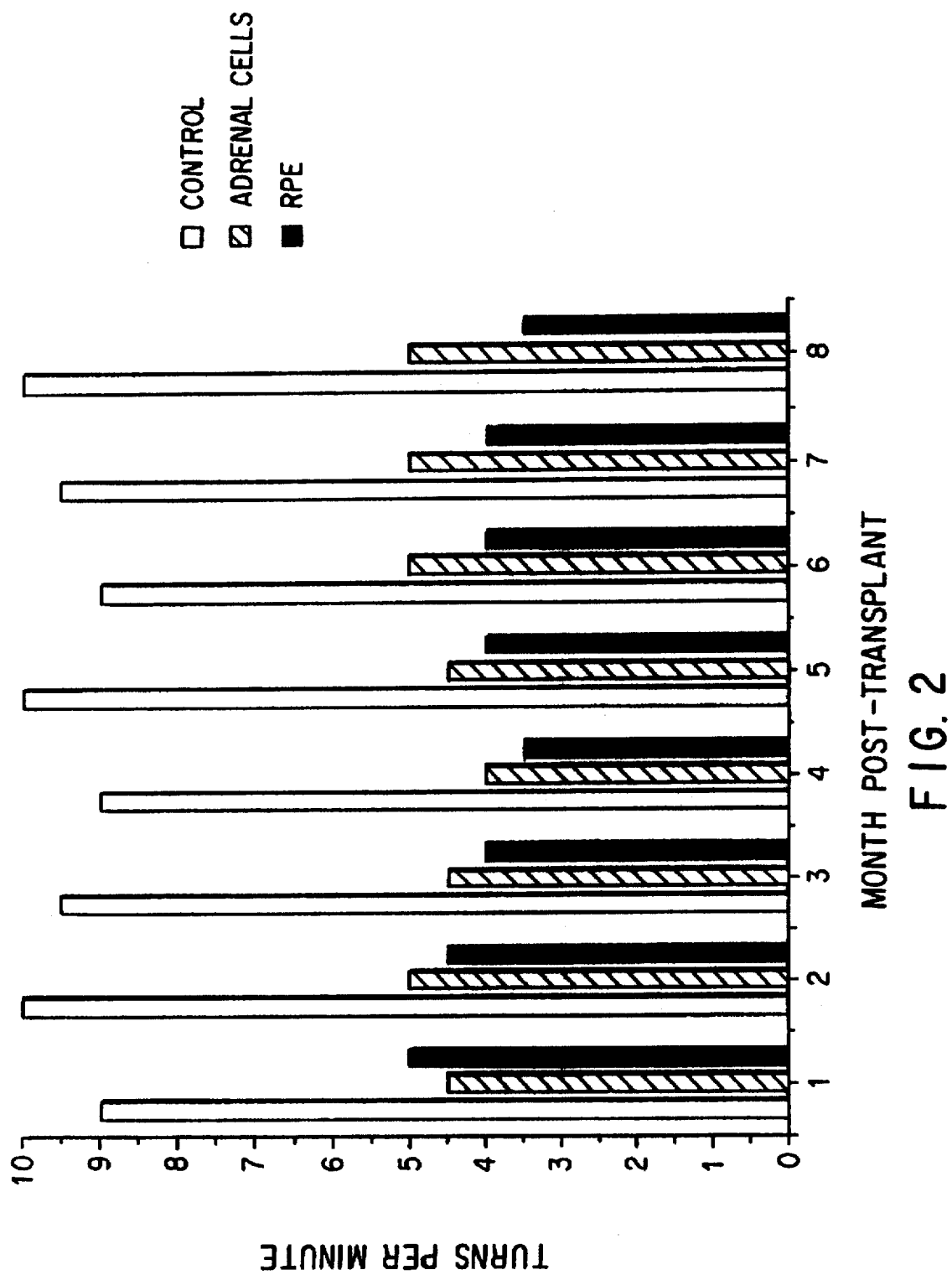
FIG. 2 is a graph showing effects of transplanting cells attached to glass beads on apomorphine-induced turning behavior in rats. Rats received either control beads, or beads to which adrenal chromaffin cells or retinal pigment epithelial (RPE) cells had been attached.

Two groups of rats served as lesion controls. One group was not treated. A second group was injected with glass beads in the putamen-caudate region. Both these control groups exhibited rotational behavior in the range of 9–10 turns/min (see FIG. 2).

When beads containing adrenal chromaffin cells were injected into the same area of the brain, an immediate reduction of the rotational behavior occurred, to a level of about 40–50% of the control values. This change represents a substantial therapeutic effect. It is noteworthy that in short-term studies using fetal cells, such as those discussed in the Background section above, similar decreases in rotation were observed. The apomorphine challenge using the present dose represents an extreme test. With lower doses of apomorphine, turning can be reduced to 0, but false positives become more frequent.

The experimental findings discussed above represent results from 8 control and 10 treated rats, exceeding the number required for statistical significance at a p value of 0.001.

Similar experiments were conducted with retinal pigment epithelial which had been cultured with beads and then injected. Similar or somewhat improved results were obtained, which may be related to the fact that these cells produce high levels of dopamine (See FIG. 2).

A second effect observed in these studies relates to the fact that 6-OHDA lesioned rats do not maintain a normal growth curve. The rats which have been implanted with adrenal chromaffin cells or retinal pigment epithelium cells on beads regain a normal growth curve.

Histological analysis of the brains of rats exhibiting no or only limited effects of the transplanted cells indicated that only a very small number of cells had been injected. In such nonresponders, injection coordinates were found to have been inaccurate. When the results of these particular animals were removed from the analysis, the average rotation after cell transplant was reduced from $9\pm0.5$ turns/min for non-transplanted controls to $5.1\pm1.2$ turns/min for transplanted rats. Statistical analysis using Student's t test yielded a p-value between 0.05 and 0.001, indicating a high level of statistical significance of this difference.

Histological examination of brains of the experimental animals showed distinct clusters of well-pigmented cells with no sign of vascular infiltrate or inflammatory reaction. The slides were further examined by Dr. Victor Sapirstein of the Nathan Kline Institute of Psychiatric Research (Orangeburg, N.Y.) who concurred in these findings.

EXAMPLE V

Lone Term Survival of Cells Transplanted into the Brain with Beads

Adrenal chromaffin cells (prepared as described in Example IV) in numbers ranging from $10^3$ to $10^7$ were injected into the caudate-putamen area of rat brains in volumes of 5–20 µl. At various times thereafter ranging from 1 to 180 days (see FIG. 3), animals were sacrificed, and their brains were sectioned into 20–50 µm sections. The sections were examined at 400× and the densities of cells were calculated from the cells/microscopic field. Results were expressed as the % of cells surviving (viable cells as a percent of injected cells). Each experimental group contained 6 rats.

Figure 3:
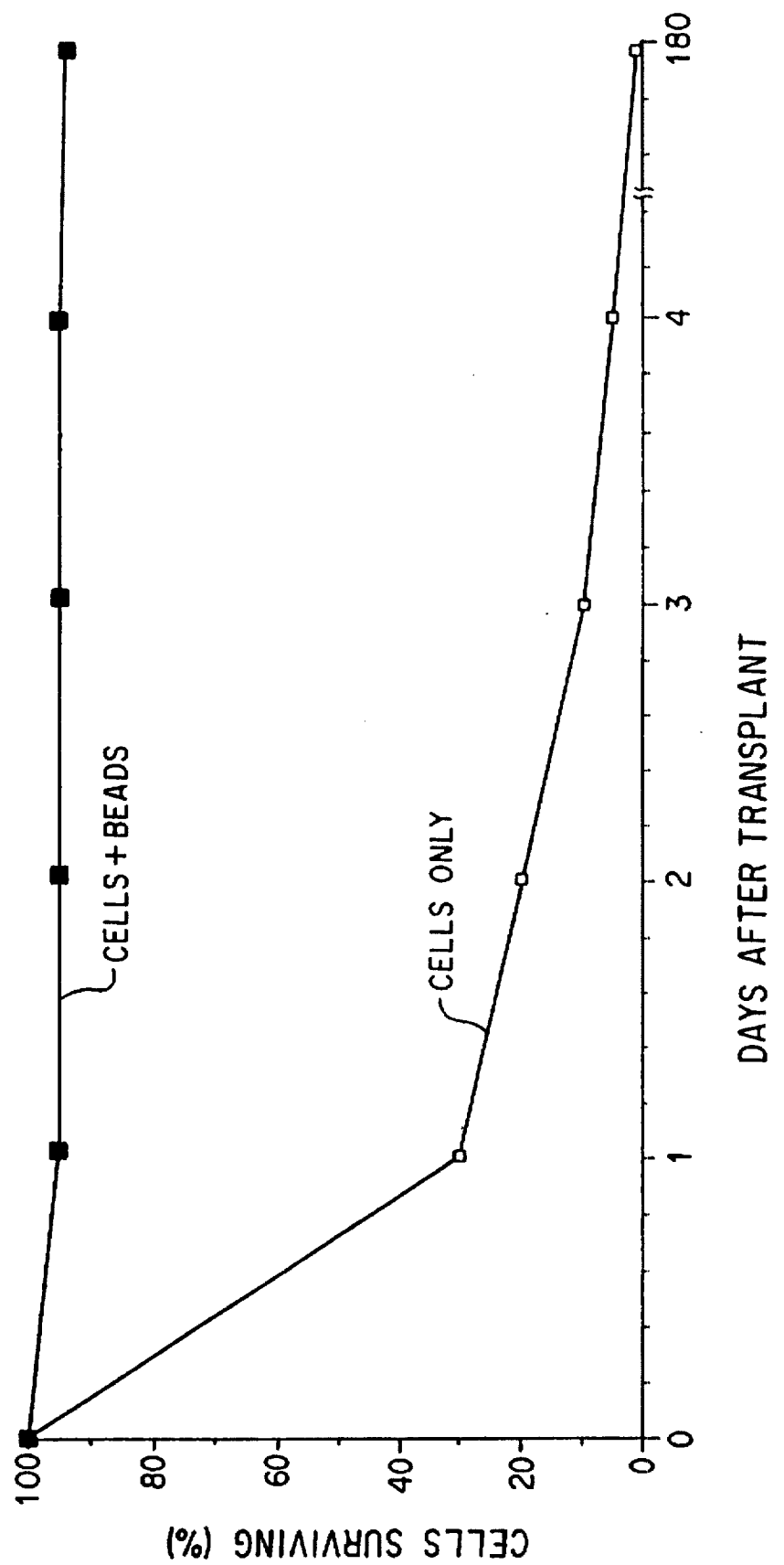
FIG. 3 is a graph showing the survival of cells, either transplanted alone or transplanted after incubation with glass beads, transplanted into rat brains.
Figure 4:
FIG. 4 is a photomicrograph showing a glass bead surrounded by associated viable pigmented adrenal chromaffin cells six months after transplantation into a rat brain (Enlargement: 400×).

The results shown in FIGS. 3 and 4 demonstrate that cells injected alone (in the absence of beads) died rapidly, with only 30% survival at 24 hours. Viability further decreased at a slower rate over the next period of days to weeks. At some time between 30 and 180 days all the implanted cells died. This observation is related with the many literature reports showing that therapeutic effects of cells transplanted into the brain greatly diminish over a few month period (see, for example, Lieberman, supra; Lindvall, supra; Bakay, R. A. E., supra).

The upper curve in FIG. 3 shows survival of cells injected after being grown on beads as described in Example IV. There was no rapid cell loss during the initial 24 hours. Furthermore, close to 100% of the injected bead-adherent cells remained viable in vivo for the entire test period of 180 days. FIG. 4 is a photomicrograph of a section of a rat brain six months after transplantation of adrenal chromaffin cells showing deeply pigmented viable cells attached to the bead and in the adjacent area.

Similar results have been obtained using retinal pigment epithelial cells (in 6 rats) in a 180 day study. In addition, similar results were also obtained in a 30 day study with human fibroblasts on beads transplanted into two rats.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A syringe containing therein viable cells that are adhered to the surface of a support matrix, wherein the viable cells are selected from the group consisting of retinal pigment epithelial cells, chromaffin cells, cells of neural origin, cells of paraneural origin, cells engineered by somatic cell hybridization and cells derived from the adrenal medulla.

2. The syringe of claim 1, wherein the support matrix is made of a material selected from the group consisting of glass, polystyrene, polypropylene, polyethylene, polycarbonate, polypentene, acrylonitrile polymer, nylon, magnetite, natural polysaccharide, a modified polysaccharide and collagen.

3. The syringe of claim 2, wherein the support matrix is glass.

4. The syringe of claim 2, wherein the support matrix is a microcarrier bead.

5. The syringe of claim 4, wherein the microcarrier bead has a diameter of from about 90 μm to about 150 μm.

6. The syringe of claim 1, wherein the cells of neural origin are neural cell lines.

7. The syringe of claim 1, wherein said viable cells are dopamine producing cells.

8. The syringe of claim 7, wherein the dopamine producing cells are selected from the group consisting of adrenal chromaffin cells and retinal pigment epithelial cells.

9. The syringe of claim 1, wherein said viable cells produce acetylcholine.

10. The syringe of claim 1, wherein said viable cells produce GABA, acetylcholine or a mixture thereof.

11. The syringe of claim 1, wherein said cells produce GABA or molecules that block excitatory amino acid pathways.

* * * * *